US005409990A

United States Patent [19]
Linnau et al.

[11] Patent Number: 5,409,990
[45] Date of Patent: Apr. 25, 1995

[54] COMPLEX CONTAINING COAGULATION FACTOR IX

[75] Inventors: Yendra Linnau; Maria Sazgary, both of Vienna, Austria

[73] Assignee: Immuno Aktiengesellschaft, Wien, Austria

[21] Appl. No.: 146,921

[22] Filed: Nov. 3, 1993

Related U.S. Application Data

[62] Division of Ser. No. 822,996, Jan. 21, 1992, Pat. No. 5,281,661.

[30] Foreign Application Priority Data

Jan. 25, 1991 [AT] Austria .................................. 163/91

[51] Int. Cl.⁶ ...................... C08G 63/48; C08G 63/91; A61K 35/14
[52] U.S. Cl. ..................................... 525/54.1; 530/381
[58] Field of Search .......................... 525/54.1; 530/381

[56] References Cited

U.S. PATENT DOCUMENTS

| | | | |
|---|---|---|---|
| 4,820,805 | 4/1989 | Neurath et al. | 530/410 |
| 5,061,789 | 10/1991 | Möller et al. | 530/381 |

FOREIGN PATENT DOCUMENTS

| | | |
|---|---|---|
| 0229026 | 7/1987 | European Pat. Off. . |
| 0159311 | 4/1989 | European Pat. Off. . |
| 0317376 | 5/1989 | European Pat. Off. . |
| 3914869 | 8/1990 | Germany . |

OTHER PUBLICATIONS

Einarsson et al., "Removal of Hepatitis B virus From A Concentrate Of Coagulation Factors II, VII, IX And X By Hydrophobic Interaction Chromatography", J. Vir. Met., 3:213-228 (1981).

Miletich et al., "The Synthesis of Sulfated Dextran Beads for Isolation of Human Plasma Coagulation Factors II, IX, and X", Anal. Biochem., 105:304-310 (1980).

H. G. J. Brummelhuis, "Preparation of the Prothrombin Complex", Methods of Plasma Protein Fractionation, ed. JM Curling, pp. 117-128, Acad. Press (1980).

Vukovich et al., "Separation of Human Blood Clotting Factors from Fibrinogen and other Plasma Proteins by Chromatography on Butyl-Sepharose", Folia Haematol, 107:1, 148-151 (1979).

Scopes, "Separation by Adsorption", Protein Purification Principles and Practice, 176-179 (1987).

A copy of the European search Report.

*Primary Examiner*—Nathan M. Nutter
*Attorney, Agent, or Firm*—Brumbaugh, Grave, Donohue & Raymond

[57] ABSTRACT

Factor IX is selectively adsorbed by means of hydrophobic chromatography from an aqueous mixture containing at least one plasma zymogen or a vitamin-K dependent protein in addition to factor IX. By this method, the efficient enrichment of factor IX for the production of pharmaceutical preparations has become possible.

8 Claims, No Drawings

COMPLEX CONTAINING COAGULATION FACTOR IX

This application is a division of application Ser. No. 07/822,996, filed on Jan. 21, 1992, and now U.S. Pat. No. 5,281,661.

The invention relates to a complex containing coagulation factor IX as well as to a process for producing a factor IX containing pharmaceutical preparation.

Coagulation factor IX is useful for replacement therapies in patients suffering from hemophilia B. This hemophilic disease results from a factor IX deficiency.

Replacement treatments are effected with factor IX concentrates additionally containing coagulation factors II, VII, IX and X (prothrombin complex). The coagulation factors contained in such concentrates are vitamin-K dependent factors and are associated with each other on account of their similar structures. However, any supply of a coagulation factor other than factor IX constitutes a load on hemophiliacs suffering from hemophilia B. For this reason, it is sought to use highly enriched factor IX concentrates in therapy as alternatives to combined preparations.

The starting material for the production of factor IX preparations is human plasma, which, however, contains only slight amounts of factor IX (4 $\mu$g/ml). To recover factor IX, not only large amounts of plasma must, therefore, be processed, but it is also necessary to eliminate any disturbing accompanying proteins as far as possible. This is rendered even more difficult because such accompanying proteins have similar physiochemical properties.

Another difficulty resides in the fact that the final product must be freed from infectious agents during work-up, because the starting material may contain, for instance, hepatitis viruses or HIV. In doing so, every single process step and every single virus inactivation procedure must be realized with a view to preserving the biologic activity of factor IX to the largest extent possible. It has been endeavored for years to find a process optimumly satisfying these requirements.

The enrichment of factor IX by simultaneously de-riching the other factors by means of chromatographic methods is, of course, the more successful the more specific the interaction of coagulation factor IX with the stationary phase.

Ion exchange and affinity chromatographic processes have already been known for the production of a factor IX containing fraction from aqueous mixtures containing factors II, VII, IX and X. According to the process described in DE-C-39 14 869, a factor IX containing fraction is obtained by initially adsorbing factor IX on an adsorbant carrying an $\alpha$-hydroxylamino group. Elution of the adsorbed factor IX is effected by increasing the amine or the salt concentration, which suggests the presence of ionic binding forces between factor IX and the adsorbant. Following this first enrichment stage, purification by means of chromatography on a matrix carrying a sulfated carbohydrate is carried out.

Affinity chromatographic methods are characterized by high specificities. Factor IX is adsorbed on a carrier material via antibodies or other groups having a high affinity to factor IX, e.g., heparin, is washed and eluted. According to the method of, for instance, EP-A-317 376, factor IX is adsorbed on immobilized heparin. The elution of factor IX is effected by increasing the salt concentration in the buffer. The same holds for antibodies against factor IX as affinity carriers.

In EP-A 229 026, factor IX is adsorbed on a hydrophobic antibody and is eluted by a salt gradient. One problem involved consists in that, under the elution conditions applied, not only factor IX is dissociated, but also heparin and antibodies, thus being contained in the end product as contaminants.

Furthermore, it is known that a coagulation factor concentrate containing factors II, VII, IX and X can be freed from virus antigens by chromatography on a hydrophobic matrix, by hydrophobically binding the said antigens to the matrix while the coagulation factors pass the matrix by preserving their biologic activity (J. Vir. Meth., 3, 213–228 (1981)).

The invention is based on the object to provide a chromatographic process that does not have the disadvantages pointed out above and by which the efficient enrichment of factor IX from an aqueous mixture containing other proteins as well, in particular plasma zymogens or vitamin-K dependent proteins, is feasible.

In accordance with the invention, a coagulation factor IX complex is provided, which comprises a carrier based on a polymer having hydrophobic groups, to which factor IX is selectively bound from an aqueous mixture containing at least one plasma zymogen in addition to factor IX. Moreover, factor IX may be present in the complex according to the invention selectively bound from an aqueous mixture containing at least one vitamin-K dependent protein, such as protein C, protein S or factors II, VII and X in addition to factor IX, or from an aqueous mixture containing a prothombin complex.

The invention is based on the finding that coagulation factor IX adsorbs, from an aqueous solution that exhibits a high conductivity, on a matrix including hydrophobic side chains selectively, i.e., in the presence of a plasma zymogen or of a vitamin-K dependent protein. This is surprising inasmuch the cited proteins possess similar physicochemical properties. The selective adsorbability of factor IX may be applied to enriching factor IX.

A preferred embodiment of the complex according to the invention is characterized in that factor IX is contained at an activity that is at least five times larger than that of another vitamin-K dependent protein present.

Preferably, the complex according to the invention is subjected to a treatment for inactivating possibly present infectious agents.

The complex according to the invention may be prepared by contacting one of the above-mentioned factor IX containing aqueous mixtures which has a conductivity of at least 30 mS, preferably of between 60 and 120 mS, with a carrier based on a polymer including hydrophobic groups in order to complex factor IX, whereupon the complex formed, if desired, is washed and, if desired, is subjected to the inactivation of possibly present infectious agents. According to the invention, factor IX, thus, is being enriched by the technique of hydrophobic chromatography. Advantageously, complex formation is carried out in the presence of a detergent.

The invention also relates to a method for producing a pharmaceutical preparation containing coagulation factor IX, which is characterized in that factor IX is eluted from the complex according to the invention, whereupon the factor IX containing eluate is processed to a pharmaceutical preparation. As is the common practice with hydrophobic chromatography, elution is carried out at a lower conductivity than is adsorption. Suitably, elution is carried out at a conductivity lower by 20% at the most.

A preferred embodiment of the method according to the invention consists in that
- plasma or a factor IX containing plasma fraction is subjected to anion exchange chromatography, wherein factor IX is bound,
- bound factor IX is eluted,
- eluted factor IX is subjected to anion exchange chromatography in the presence of a detergent, wherein factor IX is bound,
- bound factor IX is eluted,
- the factor IX containing eluate is subjected to an inactivation of possibly present infectious agents, and
- factor IX is separated by means of hydrophobic chromatography and is processed to a pharmaceutical preparation.

The complex according to the invention, furthermore, may be used for obtaining monoclonal or polyclonal antibodies that are directed against factor IX.

The invention will be explained in more detail by way of the following examples.

EXAMPLE 1

From 10 liters of human blood plasma, the prothrombin complex (coagulation factors II, VII, IX and X) is obtained by the method according to Brummelhuis (Methods of Plasma Protein Fractionation, ed. J M Curling, p. 117, Acad. Press. 1980) by adsorption on DEAE-Sephadex. 50 ml prothrombin complex (3669 I.U. factor II, 2858 I.U. factor IX and 2734 I.U. factor X) were diafiltered in order to obtain the composition of buffer A (1000 mM NaCl, 15 mM sodium citrate, pH 7).

A column containing 30 ml of a hydrophilic vinyl polymer including butyl groups (Fractogel TSK-Butyl (MERCK, Darmstadt)) is equilibrated with 100 ml buffer A and the prothrombin complex is applied at a flow rate of 360 ml/h. After washing of the packed gel with 350 ml buffer A, the factor IX containing fraction is eluted with 180 ml buffer B (400 mM NaCl).

The yield of factor IX amounted to 76% of the initial activity. The specific activity of factor IX was 19.7 I.U. factor IX/mg protein. Factors II and X were detectable at less than 20% of the initial activity.

EXAMPLE 2

50 ml prothrombin complex were chromatographed in a manner analogous to Example 1. Yet, 45 ml phenyl group containing methacrylate polymer (Toyopearl Phenyl 650M (TOSO HAAS, Stuttgart)) equilibrated with 1.4M ammonium sulfate were used as the column material. The elution of Factor IX was effected with 0.2M ammonium sulfate.

The yield of factor IX amounted to 48% of the initial activity and the specific activity was 27.2 I.U. factor IX/mg protein.

EXAMPLE 3

150 ml prothrombin complex are pre-purified by means of dextran sulfate (Miletich et al., Analytical Biochemistry 105, 304 (1980). 20 ml eluate (912 I.U. factor IX, 160 I.U. factor X) are packed on a column containing 20 ml of an agarose polymer including octyl groups (Octyl-Sepharose-CL-4B (PHARMACIA, Sweden) in the manner analogous to Example 1. Before this, the column was equilibrated with 80 ml buffer A. After washing of the packed gel with 120 ml buffer A, the factor IX containing fraction is eluted with 80 ml of a 250 mmolar NaCl solution.

The yield of factor IX amounted to 54% of the initial activity. The specific activity was 186 I.U. factor IX/mg protein. Factor X was present only in traces.

EXAMPLE 4

50 ml prothrombin complex were separated by means of hydrophobic chromatography in a manner analogous to Example 1. Immediately before being applied to 35 ml of a hydrophilic vinyl polymer containing butyl groups (Fractogel TSK-Butyl), the prothrombin complex additionally was treated with 2% of a polyoxyethylene-20-sorbitane-monooleate Tween 80 and 0.01% tri-(n-butyl)-phosphate according to the method described in U.S. Pat. No. 4,820,805.

The yield of factor IX amounted to 83% of the initial activity and the specific activity was 24.1 I.U. factor IX/mg protein.

EXAMPLE 5

2 g of the lyophilized prothrombin complex were heated at 60° C. for 10 hours according to the method described in EP-A-0 159 311 by elevating the partial water vapor pressure in order to inactivate possible pathogens. Subsequently, the hydrophobic chromatography was carried out on 20 ml of an agarose polymer containing octyl groups (Octyl-Sepharose-CL-4B).

The yield of factor IX amounted to 63% of the initial activity. The specific activity was 32 I.U. factor IX/mg protein.

What we claim is:

1. A coagulation factor IX complex which comprises a carrier based on a polymer containing hydrophobic groups, to which factor IX is selectively bound from an aqueous mixture containing at least one plasma zymogen in addition to factor IX.

2. A coagulation factor IX complex which comprises a carrier based on a polymer containing hydrophobic groups, to which factor IX is selectively bound from an aqueous mixture containing at least one vitamin-K dependent protein in addition to factor IX.

3. A coagulation factor IX complex as set forth in claim 2, wherein said at least one vitamin-K dependent protein is selected from the group consisting of protein C, protein S and factors II, VII and X.

4. A complex as set forth in claim 2, wherein said factor IX is bound from an aqueous mixture containing prothrombin complex.

5. A complex as set forth in claim 2, wherein said factor IX has an activity that is at least five times higher than that of another vitamin-K dependent protein present in said aqueous mixture.

6. A complex as set forth in claim 1 treated to inactivate possibly present infectious agents.

7. A method for using a coagulation factor IX complex, comprising the steps of:
   (a) providing a preparation containing coagulation factor IX complex which comprises a carrier based on a polymer containing hydrophobic groups, to which factor IX is selectively bound from an aqueous mixture containing at least one plasma zymogen in addition to factor IX, and
   (b) using the complex of step (a) for obtaining monoclonal antibodies directed against factor IX.

8. A method for using a coagulation factor IX complex, comprising the steps of:

(a) providing a preparation containing coagulation factor IX complex which comprises a carrier based on a polymer containing hydrophobic groups, to which factor IX is selectively bound from an aqueous mixture containing at least one plasma zymogen in addition to factor IX, and (b) using the complex of step (a) for obtaining polyclonal antibodies directed against factor IX.

* * * * *